US011376226B2

United States Patent
Kim et al.

(10) Patent No.: US 11,376,226 B2
(45) Date of Patent: Jul. 5, 2022

(54) BIODEGRADABLE POLYMER MICROPARTICLE CONTAINING STEROID DRUG AND PREPARATION METHOD THEREFOR

(71) Applicant: REGENBIOTECH, INC., Daejeon (KR)

(72) Inventors: Jeoung Yong Kim, Seoul (KR); Won Chun Lee, Daejeon (KR); Mi Yeon Kang, Daejeon (KR); Hang Je Choi, Daejeon (KR)

(73) Assignee: REGENBIOTECH, INC., Daejeon (KR)

( * ) Notice: Subject to any disclaimer, the term of this patent is extended or adjusted under 35 U.S.C. 154(b) by 107 days.

(21) Appl. No.: 16/756,306

(22) PCT Filed: Jan. 9, 2020

(86) PCT No.: PCT/KR2020/000413
§ 371 (c)(1),
(2) Date: Apr. 15, 2020

(87) PCT Pub. No.: WO2020/189886
PCT Pub. Date: Sep. 24, 2020

(65) Prior Publication Data
US 2021/0212956 A1    Jul. 15, 2021

(30) Foreign Application Priority Data

Mar. 19, 2019 (KR) .................. 10-2019-0031072
Dec. 31, 2019 (KR) .................. 10-2019-0179090

(51) Int. Cl.
*A61K 9/51*    (2006.01)
*A61K 9/00*    (2006.01)
(Continued)

(52) U.S. Cl.
CPC .......... *A61K 9/5192* (2013.01); *A61K 9/0019* (2013.01); *A61K 9/5153* (2013.01);
(Continued)

(58) Field of Classification Search
None
See application file for complete search history.

(56) References Cited

U.S. PATENT DOCUMENTS 4,530,840 A * 7/1985 Tice .................. A61P 29/00
514/179
5,876,756 A * 3/1999 Takada ................ A61K 31/495
424/489
(Continued)

FOREIGN PATENT DOCUMENTS

JP      2005-525403 A    8/2005
KR  10-2007-0107941 A   11/2007
(Continued)

OTHER PUBLICATIONS

Solvent Miscibility Chart. https://s3-us-west-2.amazonaws.com/oww-files-public/b/b0/Solvent_miscibility_chart.jpg accessed Dec. 21, 2021, 1 page. (Year: 2021).*

*Primary Examiner* — Isaac Shomer
(74) *Attorney, Agent, or Firm* — Rothwell, Figg, Ernst & Manbeck, P.C.

(57) ABSTRACT

Biodegradable polymer microparticles bearing a steroid drug and a preparation method therefor. In the method, a steroid drug and a biodegradable polyester-based polymer are dissolved in an organic solvent and sprayed into a low-temperature hydrocarbon solution to form frozen microparticles that are then immersed in a low-temperature, aqueous salt solution to deprive the microparticles of the organic solvent, thereby preparing biodegradable polymer microparticles bearing a steroid drug. The steroid drug or steroid sex hormone drug-bearing biodegradable polymer microparticles were found to have excellent biocompatibility, biodegradability, porosity, and mechanical strength and to release the steroid drug or steroid sex hormone drug for a long period of time.

4 Claims, 12 Drawing Sheets

(51) Int. Cl.
  *A61K 31/567* (2006.01)
  *A61K 31/573* (2006.01)
  *B01J 37/32* (2006.01)

(52) U.S. Cl.
  CPC .......... *A61K 31/567* (2013.01); *A61K 31/573* (2013.01); *B01J 37/32* (2013.01)

(56) References Cited

U.S. PATENT DOCUMENTS

| | | |
|---|---|---|
| 8,192,655 B2 | 6/2012 | Han et al. |
| 8,329,856 B2 * | 12/2012 | Kim .......................... B29B 9/12 528/481 |
| 8,828,440 B2 | 9/2014 | Bodick et al. |
| 2006/0083778 A1 | 4/2006 | Allison et al. |
| 2011/0217341 A1 * | 9/2011 | Sah ...................... A61K 31/137 424/400 |
| 2011/0245456 A1 * | 10/2011 | Kim ...................... C08G 63/06 528/361 |
| 2014/0072531 A1 | 3/2014 | Kim et al. |

FOREIGN PATENT DOCUMENTS

| | | |
|---|---|---|
| KR | 10-2009-0131975 A | 12/2009 |
| KR | 10-2010-0131244 A | 12/2010 |
| KR | 10-1105292 B1 | 1/2012 |
| KR | 10-2013-0093101 A | 8/2013 |
| KR | 10-1481859 B1 | 1/2015 |
| KR | 10-2017-0001403 A | 1/2017 |
| KR | 10-2018-0018892 A | 2/2018 |

\* cited by examiner

* 8h HPLC

BIODEGRADABLE POLYMER MICROPARTICLE CONTAINING STEROID DRUG AND PREPARATION METHOD THEREFOR

CROSS-REFERENCE TO RELATED APPLICATIONS

This application is a 35 U.S.C. 371 National Phase Entry Application from PCT/KR2020/000413, filed on Jan. 9, 2020, designating the U.S. and which claims priority to and the benefits of Korean Patent Application No. 10-2019-0031072, filed with the Korean Intellectual Property Office on Mar. 19, 2019, and Korean Patent Application No. 10-2019-0179090, filed with the Korean Intellectual Property Office on Dec. 31, 2019, the entire contents of which are incorporated herein by reference.

TECHNICAL FIELD

The present disclosure relates to a biodegradable polymer particle containing a steroid drug and a preparation method therefor.

BACKGROUND ART

Until recently, pharmacological research has been focused on the development of novel drugs to increase therapeutic effects on new diseases or diseases that are difficult to cure with conventional drugs. However, difficulty in developing novel drugs, a risk of high investment costs, and a difference between practical laboratory research results and clinical application results allow only some major international bioengineering companies to perform related research and development, with the limitative permission of domestic companies to do so. In addition to the development of novel drugs, a need for research and development of drug delivery is arising as approaches of delivering drugs to practical diseased sites have been proven to have a significant effect on the treatment of disease in various studies.

A drug delivery system refers collectively to a series of technologies that enables the introduction of a pharmacologically active substance into the body and allows for optimal efficacy of the drug by controlling the delivery and release thereof into cells, tissues, and organs in the body with the aid of various physicochemical approaches. Oral capsules and tablets that are designed to control delivery rates of drugs by adjusting dissolution rates in body fluid after entry into the human body account for the most basic drug delivery system. This is now the most popular commercialized technique in which drugs are released and absorbed into the body during the dissolution of polymer materials in water. In addition, a matrix approach, obtained by mixing a drug with a biocompatible polymer, for drug delivery, a biodegradable delivery device using a biodegradable polymer to control drug delivery rates depending on degradation rates, and a hydrogel delivery system in which drug delivery is controlled using the dependence of swelling on the temperature, pH, and electrical strength of the environment of the implant have been developed.

Drug delivery particles are fabricated to range in size from tens nanometers (nm) to hundreds micrometers (μm). At first, the particles were used principally in an emulsion manner, but recently, research has been directed toward an improvement in the uniformity of particle sizes by using a microfluidic system or a micro- or nanotemplate or toward the fabrication of particles of various shapes other than simple spherical particles (Ryu Won Hyoung, 2012).

Steroids are used as drugs having potent anti-inflammatory and immunomodulatory effects and applied to various diseases including rheumatoid arthritis. Providing a practical perception that the long-term and high-dose use of steroids causes side effects and a resistance thereto while the therapeutic effects are vanished with the reduction of dose, steroids are considered to be used temporarily for palliating symptoms. Most side effects tend to be proportional to the dose and duration of steroids. Therefore, there is a need for a technique that enables steroids to modulate inflammations with minimum side effects.

Sex hormones, which belong to steroids, are released directly to blood and then exhibit physiological activities specific for generative functions. Testosterone, which is a male sex hormone, is responsible for the development of secondary sexual characteristics of men, and performs the role of promoting the production of sperms, developing male reproductive organs such as prostate and seminal vesicles, and increasing muscles. Estrogen, which is the primary female sex hormone, is responsible for the development and regulation of the female reproductive system and secondary sex characteristics such as uterine growth and lactation. Progesterone makes the endometrium thick to prepare the uterus for implantation and also acts to maintain pregnancy.

The secretion of sex hormones is regulated by the hypothalamus and the pituitary. When the hypothalamus stimulates the anterior pituitary, follicle stimulating hormone and luteinizing hormone are released from the pituitary, promoting the secretion of male and female sex hormones. Insufficiency of sex hormones causes women to suffer from menstrual irregularity and dysmenorrhea, irregular menstrual cycles, insufficient height and breast development, skin troubles, hypoactive sexual desire disorder and anorgasmia, reduced vaginal contraction, premature menopause and menopausal disorder, skin senescence, depression, nervousness, dyspareunia, urinary incontinence, decreased vaginal discharges, menopause, osteoporosis, infertility, and various female disorders (Choi, D. S., et al., 2012) and causes hypoactive sexual desire disorder, hypogonadism, a sensation of fatigue, depression, lethargy, decreased muscle, dynapenia, abdominal obesity, skin senescence, a decrease of bone density, and memory decline in men, having adverse influence on the quality of life (Min, K. S., et al., 2011).

Hormone replacement therapy (HRT) is used as a simple method for alleviating symptoms and disorders caused by insufficient sex hormones. The medications used in hormone replacement therapy may be selected depending the convenience of administration, patient's preference and age, cost, and the degree or state of side effects. Other important parameters for selecting the medications include whether the hormone is maintained at a physiological level after administration and whether the hormone is increased to a non-physiological level. Oral formulations, agents for external use, such as gel formulations and patches, and injections are generally used. All of them are stable and effective, but retain advantages and disadvantages according to administration routes and medications (Min, K. S., et al., 2011).

Oral formulations are the most popular because they are the most convenient to administer and the most inexpensive. When orally administered, hormones are absorbed into the gastrointestinal tract, metabolized in the liver, and transferred into blood to act functions thereof. After gastrointestinal absorption and hepatic metabolism, the orally administered hormones decrease in bioavailability. An increased dose for compensating for the decreased bioavailability increases the amount of by-products generated through the hepatic metabolism, which would lead to an increased risk of generating side effects. To avoid the risk, the user should bear the disadvantage of taking the formulation at a low dose many times a day.

An agent for external use was developed for convenience of administration and for compensation for the injection's disadvantage of reaching a non-physiological, high blood level. When administered transdermally, a hormone is introduced into blood stream through skin in a simple diffusion manner and thus can increase a therapeutic effect while avoiding hepatic actions. A patch, which is a kind of agent for external use, is usually applied for 24-48 hours and can reach and maintain a blood hormone level within a physiological level range for several days. A patch is also advantageous in that a blood hormone level can be easily decreased within several hours after removal of the patch. However, side effects such as itching and rubefaction may occur at the surface on which a patch is applied. Gel formulations are much used thanks to their advantages of being uniformly absorbed, maintaining a uniform physical hormone concentration, being easy to apply, and being almost free of skin irritation. However, the large amount to be applied is an inconvenient matter and when the user contacts with another person, the medicament ingredient may be transferred thereto.

A hormonal injection, which is the longest used method, is advantageously not administered every day. However, there is a very violent modulation in blood hormone level within a short term as the concentration of the hormone peaks to a non-physiologically high blood level just after injection and is reduced to a sub-normal level with the lapse of time. Particularly, the non-physiological, high hormone level just after injection may incur a significant side effect.

In order to overcome such disadvantages, there is therefore a need for developing a formulation that allows the administered sex hormone to act for a long period of time and release slowly to reduce side effects caused by a rapid increase in blood hormone level.

In recent years, drug delivery systems in which drugs are supported by polymer particles have been developed. However, the method in which a drug is mixed with an adhesive and adsorbed onto the surface of polymer particles has a difficulty in maintaining drug release as the drug adsorbed onto the polymer surface is rapidly released in the early stage. In addition, the deposition approach in which polymer particles are immersed in a drug so that the drug permeates the particles exhibits the disadvantage that the drug is irregularly released according to the structures of the polymer particles.

Leading to the present disclosure, inventive research and development, conducted by the present inventors, into drug formulations resulted in the finding that biodegradable microparticles bearing steroid drugs or sex hormone drugs can uniformly release the drugs over the period of degradation thereof and can be controlled to release the drugs for a long period of time.

As for related arts, reference may be made to Korean Patent Number 1105292, issued to the present inventors, which discloses biodegradable polymeric microparticles for tissue regeneration, which are prepared by dissolving biodegradable polyester-based polymer in DMSO, spraying the solution into a chilled hydrocarbon solution to obtain frozen DMSO microparticles, and immersing the DMSO microparticles in a chilled aqueous salt solution to melt DMSO. However, the document pertains to the use of the biodegradable polymeric microparticles as a cell carrier in which cells are grown, and does not give any description of the long-term release of a drug from the biodegradable polymeric microparticles in a sustained manner. In addition, Korean Patent Publication Number 2007-0107941 A discloses a biodegradable microsphere composition for controlled release of growth hormone, but differs from the present disclosure in terms of the configuration and preparation method of biodegradable polymeric microparticles. U.S. Pat. No. 4,530,840 discloses microparticles bearing an anti-inflammatory agent and a preparation method therefor, but differs from the present disclosure in terms of the preparation method for biodegradable polymeric microparticles.

DETAILED DESCRIPTION OF THE INVENTION

Technical Problem

A purpose of the present disclosure is to provide biodegradable polymeric microparticles bearing a steroid drug or a sex steroid hormone drug and a preparation method therefor.

Technical Solution

The present disclosure pertains to a method for preparing biodegradable polymeric microparticles bearing a steroid drug, the method comprising the steps of: (a) dissolving a mixture of a steroid drug and a biodegradable polyester-based polymer in an organic solvent to give a solution containing the steroid drug and the biodegradable polyester-based polymer; (b) spraying the solution containing the steroid drug and the biodegradable polyester-based polymer therein to a hydrocarbon solution of C5-10 maintained at a temperature of less than the melting point of the organic solvent to form microparticles; (c) adding the microparticles to an aqueous salt solution to dissolve and eliminate the organic solvent; and (d) desalting the organic solvent-eliminated microparticles.

In step (a), the mixture of the steroid drug and the biodegradable polyester-based polymer may be dissolved in an amount of 1-25% (w/v) in the organic solvent, based on the total volume of the solution.

In step (a), the mixture may comprise the steroid drug and the biodegradable polyester-based polymer at a weight ratio of 1:99 to 3:7.

The steroid drug may be at least one selected from the group consisting of deflazacort, desonide, desoximetasone, dexamethasone, diflorasone, diflucortolone, difluprednate, loteprednol etabonate, rimexolone, mazipredone, medrysone, methylprednisolone, meprednisone, mometasone furoate, beclomethasone, betamethasone, budesonide, algestone, alclometasone, amcinonide, enoxolone, corticosterone, cortisone, cortivazol, chloroprednisone, clobetasol, clobetasone, clocortolone, cloprednol, tixocortol, triamcinolone, triamcinolone acetonide, triamcinolone benetonide, triamcinolone hexacetonide, paramethasone, pregnenolone acetate, prednicarbate, prednisolone, prednisolone 25-diethylaminoacetate, prednisolone sodium phosphate, prednisone, prednival, prednylidene, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, and a sex hormone.

The sex hormone may be at least one selected from the group consisting of progesterone, testosterone, estrogen, androgen, estradiol, levonorgestrel, gestodene, desogestrel, dienogest, cyproterone acetate, and ethynyl estradiol.

The biodegradable polyester-based polymer may be at least one selected from the group consisting of poly-lactic acid (PLA), poly-glycolic acid (PGA), poly-D,L-lactide (PDLLA), poly(D,L-lactic-co-glycolic acid (PLGA), poly-carprolactone (PCL), poly(valerolactone), poly(hydroxyl butylate), and poly(hydroxy valerate).

The biodegradable polyester-based polymer may have a weight average molecular weight of 10,000-250,000.

The organic solvent may be at least one selected from the group consisting of DMSO (dimethyl sulfoxide), PCL (poly caprolactone), chloroform, acetone, dichloromethane, benzene, toluene, isopropyl ether, chlorobenzene, ethylene carbonate, and ethylene glycol.

In step (b), the hydrocarbon of C5-10 may be at least one selected form the group consisting of pentane, hexane, hepatane, octane, nonane, decane, and petroleum ether.

In step (c), the aqueous salt solution may be a 5-30% (w/v) solution of NaCl or $CaCl_2$) in water.

The biodegradable polymeric microparticles bearing a steroid drug may have a diameter of 10-1000 μm.

The present disclosure pertains to biodegradable polymeric microparticles bearing a steroid drug, which are prepared using the preparation method.

In addition, the present disclosure pertains to an antiinflammatory composition comprising the biodegradable polymeric microparticles bearing a steroid drug.

Furthermore, the present disclosure pertains to a steroid drug formulation comprising the biodegradable polymeric microparticles bearing a steroid drug.

The sex hormone formulation may be an injection.

Below, a detailed description will be given of the present disclosure.

The present disclosure pertains to a method for preparing biodegradable polymeric microparticles bearing a steroid drug, the method comprising the steps of: (a) dissolving a mixture of a steroid drug and a biodegradable polyester-based polymer in an organic solvent to give a solution containing the steroid drug and the biodegradable polyester-based polymer; (b) spraying the solution containing the steroid drug and the biodegradable polyester-based polymer therein to a hydrocarbon solution of C5-10 maintained at a temperature of less than the melting point of the organic solvent to form microparticles; (c) adding the microparticles to an aqueous salt solution to dissolve and eliminate the organic solvent; and (d) desalting the organic solvent-eliminated microparticles.

As a rule, organic solvents are highly miscible with each other. For this reason, microparticles cannot be prepared by spraying one organic solvent to a different solvent (hereinafter, organic solvent A and organic solvent B). As soon as a solution of a polymer in organic solvent A is sprayed to and thus brought into contact with organic solvent B, the two organic solvents are miscible with each other, which makes it impossible to freeze organic solvent A and thus to prepare microparticles.

However, although both being usual organic solvents, the organic solvents and the hydrocarbons available in the present disclosure are immiscible with each other because of a great difference in polarity therebetween. In addition, the organic solvents are available because they can well dissolve the steroid drug/biodegradable polyester-based polymer mixture. The organic solvents are very miscible with water. In this condition, when frozen particles are added to water, the organic solvent is easily dissolved out whereas the biodegradable polyester-based polymer dissolved in the organic solvent is not dissolved in water, thereby forming microparticles in the same morphologies as are frozen in the organic solvent.

The organic solvent may be at least one selected from the group consisting of DMSO (dimethyl sulfoxide), PCL (poly caprolactone), chloroform, acetone, dichloromethane, benzene, toluene, isopropyl ether, chlorobenzene, ethylene carbonate, and ethylene glycol, preferably from the group consisting of DMSO, PCL, and chloroform, and more preferably from the group consisting of DMSO and chloroform, with the most preference for DMSO, but is not limited thereto.

Usually, microparticles are prepared using emulsification-solvent evaporation. However, this method is of procedural complexity, such as using a surfactant, exhibits a limitation in the size control of microparticles, and has a difficulty in controlling porosity of microparticles. However, the preparation method of the present disclosure can easily control the porosity because the porosity is determined depending on the concentration at which the sex hormone drug/biodegradable polyester-based polymer mixture is dissolved in the organic solvent. In the method of the present disclosure, sizes of microparticles can be easily controlled by adjusting amounts of the solution and air fed when the solution of the sex hormone drug/biodegradable polyester-based polymer mixture in the organic solvent is sprayed. Furthermore, the preparation method of the present disclosure is of simplicity and high productivity because the preparation is conducted by merely spraying the solution.

In step (a), the steroid drug/biodegradable polyester-based polymer mixture may be dissolved in an amount of 1-25% (w/v) in the organic solvent, based on the total volume of the solution prepared in step (a). Less than 1% (w/v) of the steroid drug/biodegradable polyester-based polymer mixture makes the microparticles too weak in mechanical strength to have practical utility. On the other hand, when the steroid drug/biodegradable polyester-based polymer mixture is used at a concentration higher than 25% (w/v), the production efficiency becomes poor due to the increased viscosity, as exemplified by the formation of fibers upon spraying.

In step (a), the steroid drug and the biodegradable polyester-based polymer may be mixed at a weight ratio of 1:99 to 3:7. When the amount of the steroid drug exceeds 30% by weight of the mixture, the insufficient contribution of the biodegradable polyester-based polymer to the mechanical strength may make the microparticles morphologically crushed or aggregated.

In step (b), the hydrocarbon solution should not be frozen at 0° C. or less and should exhibit phase separation from the organic solvent. Preferable is a hydrocarbon of 5-10 carbon atoms (C5-10).

The hydrocarbon of C5-10 may be at least one selected from the group consisting of pentane, hexane, hepatane, octane, nonane, decane, and petroleum ether, with preference for hexane. Hexane can be easily removed during a lyophilization or natural drying procedure due to the high volatility thereof.

Hydrocarbons of less than 5 carbon atoms are very volatile, making it difficult to prepare the microparticles. Given more than 10 carbon atoms, the hydrocarbons are impracticable and thus unfavorable.

The temperature of the hydrocarbon solution may be maintained at a temperature less than the melting point of the organic solvent in order to freeze the organic solvent. For example, when the organic solvent is DMSO, the hydrocarbon solution is preferably maintained at a temperature of less than about 18° C. under one atmospheric pressure, more preferably at a temperature of −20 to 0° C., and most preferably at a temperature of −10 to −5° C.

The melting point of the organic solvent can be adjusted depending on the contents and kinds of solutes dissolved in the organic solvent. For example, when chloroform is used as the organic solvent, its melting point is −63.5° C. When the steroid drug and the biodegradable polymer of the present disclosure are dissolved in the solvent, the solution may be frozen even at −5° C.

In step (b), the solution containing the steroid drug and the biodegradable polyester-based polymer therein in step (a) is sprayed into the hydrocarbon solution of C5-10 by applying a pressure thereto to form microparticles bearing the steroid drug.

In the present disclosure, the spraying is carried out using a commercialized nozzle. So long as it can spray the air and the solution containing the steroid drug and the biodegradable polyester-based polymer and can control amounts of the sprayed air and solution, any spraying method is available in the present disclosure without limitations thereto. Preferable is a spraying method into cryogenic fluid.

In the spraying step, the solution containing the steroid drug and the biodegradable polyester-based polymer may be sprayed at a rate of 0.2-20.0 g/min while the spraying rate of air is adjusted within 1.0 to 30.0 l/min, thereby making it easy to control sizes of the microparticles.

By phase separation and freezing, the microparticles formed in step (b) can retain their morphology and can be settled while being in a frozen state. The organic solvent used to dissolve the steroid drug/biodegradable polyester-based polymer mixture accounts for the most part in the frozen microparticles. The removal of the organic solvent from the microparticles is removed through the following step using an aqueous salt solution.

In step (c), the aqueous salt solution is preferably maintained in a non-frozen state at 0° C. or less. The removal of the organic solvent may be achieved using water. However, the organic solvent is preferably removed using an aqueous salt solution maintained at 0° C. or less in order to stabilize the microparticles.

The aqueous salt solution may be an aqueous NaCl or $CaCl_2$) solution, preferably an aqueous 5-30% (w/v) NaCl or $CaCl_2$) solution, and more preferably an aqueous 20-25% (w/v) NaCl solution.

The aqueous salt solution may be maintained at a temperature of −20 to 0° C. When the temperature is below −20° C., the aqueous salt solution is frozen and thus is impossible to use. When applied, the aqueous salt solution having a temperature higher than 0° C. causes the microparticles to become poor in stability and aggregate, thereby decreasing productivity.

In step (d), the desalting is to deprive the microparticles of the salts derived from the aqueous salt solution used to remove the organic solvent from the microparticles.

The desalting can be achieved by diluting with an excess of water, preferably, with deionized distilled water.

Designed to take advantage of phase separation between the organic solvent dissolving a steroid drug and a biodegradable polyester-based polymer and the hydrocarbon which is used as a freezing organic solvent, the preparation method for biodegradable polymer microparticles bearing a drug according to the present disclosure is easier, more effective, and simpler in mass production, compared to conventional methods. In addition, the method of the present disclosure can easily adjust sizes of the microparticles which can be thus made to be introduced into the body by injection.

Examples of the steroid drug include, but are not limited to, deflazacort, desonide, desoximetasone, dexamethasone, diflorasone, diflucortolone, difluprednate, loteprednol etabonate, rimexolone, mazipredone, medrysone, methylprednisolone, meprednisone, mometasone furoate, beclomethasone, betamethasone, budesonide, algestone, alclometasone, amcinonide, enoxolone, corticosterone, cortisone, cortivazol, chloroprednisone, clobetasol, clobetasone, clocortolone, cloprednol, tixocortol, triamcinolone, triamcinolone acetonide, triamcinolone benetonide, triamcinolone hexacetonide, paramethasone, pregnenolone acetate, prednicarbate, prednisolone, prednisolone 25-diethylaminoacetate, prednisolone sodium phosphate, prednisone, prednival, prednylidene, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, and a sex hormone.

Preferably, the steroid drug may be at least one selected from the group consisting of deflazacort, desonide, desoximetasone, dexamethasone, diflorasone, diflucortolone, difluprednate, loteprednol etabonate, rimexolone, mazipredone, medrysone, methylprednisolone, meprednisone, mometasone furoate, beclomethasone, betamethasone, budesonide, algestone, alclometasone, amcinonide, enoxolone, corticosterone, cortisone, cortivazol, chloroprednisone, clobetasol, clobetasone, clocortolone, cloprednol, tixocortol, triamcinolone, triamcinolone acetonide, triamcinolone benetonide, triamcinolone hexacetonide, paramethasone, pregnenolone acetate, prednicarbate, prednisolone, prednisolone 25-diethylaminoacetate, prednisolone sodium phosphate, prednisone, prednival, prednylidene, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, and a sex hormone.

Any sex hormone that is used in the art is available as a sex hormone drug in the present disclosure. The sex hormone drug may be preferably at least one selected from the group consisting of progesterone, testosterone, estrogen, androgen, estradiol, levonorgestrel, gestodene, desogestrel, dienogest, cyproterone acetate, and ethynyl estradiol and more preferably at least one selected from progesterone, testosterone, estradiol, estrogen, and ethynyl estradiol.

The biodegradable polyester-based polymer may be at least one selected from the group consisting of poly-lactic acid (PLA), poly-glycolic acid (PGA), poly-D,L-lactide (PDLLA), poly(D,L-lactic-co-glycolic acid (PLGA), polycarprolactone (PCL), poly(valerolactone), poly(hydroxyl butylate), poly(hydroxy valerate), and a derivative thereof. Preferably, the biodegradable polyester-based polymer may be at least one selected from the group consisting of polylactic acid, poly-glycolic acid, poly-D,L-lactide, and poly (D,L-lactic-co-glycolic acid) and more preferably poly(D, L-lactic-co-glycolic acid).

The biodegradable polyester-based polymer may have a weight average molecular weight of 10,000 to 250,000.

However, the control of sizes of the microparticles is not limited by the weight average molecular weight of biodegradable polyester-based polymer because the preparation method for microparticles according to the present disclosure allow spherical microparticles to be easily prepared and can easily control sizes of the microparticles.

Diameters of the biodegradable polymer microparticles bearing a steroid drug according to the present disclosure can be appropriately adjusted depending on concentrations of the steroid drug and the biodegradable polyester-based polymer in the organic solvent, spray amounts into the hydrocarbon solution, and spray amounts of air. In detail, a higher concentration of the biodegradable polyester-based polymer in the solution containing the steroid drug and the biodegradable polyester-based polymer or a more spray amount of the solution into the hydrocarbon solution with a lower amount of sprayed air makes a larger diameter of the microparticles.

The biodegradable polymer microparticles bearing a steroid drug may range in diameter from 10 to 1000 µm.

The biodegradable polymer microparticles bearing a steroid drug allows the steroid drug to be released over a long period of time in vivo. For example, just after a steroid drug or a sex hormone drug is conventionally injected, the level thereof in the blood drastically increases, but rapidly drops. For a therapeutic effect, a steroid drug may be repetitively administered at a high dose. In this regard, drug resistance may arise, together with side effects. When the steroid drug is a sex hormone drug, such repetitive administration may cause rapid fluctuations of blood hormone levels, which results in repeating hypo- and hypersexuality. A rapid increase of blood sex hormone level may incur hepatotoxicity. In contrast, when injected, the biodegradable polymer microparticles bearing a steroid drug according to the present disclosure are slowly degraded in blood to prevent a drastic increase of the blood steroid or sex hormone level. In addition, the steroid drug or sex hormone is slowly and uniformly released for a long period of time during which the biodegradable polymer microparticles are degraded, whereby a long acting effect can be obtained even after one dose. Therefore, the biodegradable polymer microparticles bearing a steroid drug or sex hormone therein according to the present disclosure allows the long-term release of the steroid drug or sex hormone even after one injection thereof, thereby reducing the inconvenience of many rounds of injections repeated within a short time and preventing side effects caused by drastic fluctuations of the steroid drug or sex hormone.

The release of the steroid drug carried by the biodegradable polymer microparticles differs depending on the biodegradable polymer. For example, poly(D,L-lactic-co-glycolic acid), which is used as a biodegradable polymer in the present disclosure, differs in degradation period, depending on the ratio between the lactic acid and the glycolic acid therein. In detail, the degradation period accounts for 5-6 months at the ratio of lactic acid to glycolic acid 85:15, for 3-4 months at the ratio of 75:25, and for 1-2 months at the ratio of 50:50 (Velasco, M. A., et al., 2015).

The biodegradable polymer microparticles bearing a drug according to the present disclosure can release the steroid drug over at least one months.

The biodegradable polymer microparticles bearing a steroid drug may be incubated to contain cells therein and as such, can be used as a cell carrier in an injectable form.

Also, the present disclosure provides biodegradable polymer microparticles bearing a steroid drug, prepared using the preparation method.

In addition, the present disclosure provides an inflammatory composition or a sex hormone formulation comprising the biodegradable polymer microparticles bearing a steroid drug.

The anti-inflammatory composition may be a pharmaceutical composition for prevention or treatment of inflammatory disease, the composition comprising the biodegradable polymer microparticles bearing a steroid drug and a pharmaceutically acceptable excipient.

The sex hormone formulation may be a pharmaceutical composition for preventing or treating a symptom or disease caused by the insufficiency or deficit of a sex hormone, the composition comprising the steroid sex hormone drug.

The pharmaceutical composition according to the present disclosure may be formulated into oral dosage forms, such as powders, granules, tablets, capsules, suspensions, emulsions, syrups, aerosols, and the like, agents for external use, suppositories, and sterile injection solutions, and may further comprise suitable carriers, excipients, and diluents that are typically used. Examples of the carrier, excipients, and diluents available in the composition of the present invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oils, but are not limited thereto. For formulation, a typically used diluent or excipient such as a filler, a thickener, a binder, a humectant, a disintegrant, a surfactant, etc. may be employed. Solid preparations for oral dosage include tablets, pills, powders, granules, capsules, and the like and are formulated by admixing at least one excipient, such as starch, calcium carbonate, sucrose, lactose, gelatin, etc. with the sex hormone drug-bearing biodegradable polymer microparticles. In addition, a lubricant such as magnesium stearate, talc, etc. may be used in addition to a simple excipient. Among liquid preparations intended for oral administration are suspensions, solutions for internal use, emulsions, syrups, and the like. Plus a simple diluent, such as water or liquid paraffin, various excipients, such as humectants, sweeteners, aromatics, preservatives, and the like may be contained in the liquid preparations. Also, the pharmaceutical composition of the present disclosure may be in a parenteral dosage form such as sterile aqueous solutions, non-aqueous solvents, suspensions, emulsions, lyophilizates, suppositories, and the like. Propylene glycol, polyethylene glycol, vegetable oils such as olive oil, and injectable esters such as ethyl oleate may be suitable for the non-aqueous solvents and suspensions. The basic materials of suppositories include Witepsol, Macrogol, Tween 61, cacao butter, laurin butter, glycerol, and gelatin.

The dose of the pharmaceutical composition may vary depending on the age, sex, and weight of the subject to be treated, the pathological state of the disease, the severity of the disease, the route of administration, and the judgement of the attending physician.

The pharmaceutical composition according to the present disclosure may be administered via various routes to mammals such as rats, mice, livestock, and humans. All modes of administration may be expected, for example, by oral, rectal or intravenous, intramuscular, subcutaneous, intrauterine or intracerebroventricular injections, or topical application.

Examples of the inflammatory disease include allergic disease, inflammatory bowel disease, atherosclerosis, inflammatory collagen vascular disease, glomerulonephritis, inflammatory skin disease, sarcoidosis, retinitis, gastritis, hepatitis, enteritis, arthritis, tonsillitis, laryngopharyngitis, bronchitis, pneumonia, pancreatitis, sepsis, pressure sore, degenerative chronic inflammatory disease, nephritis, calcific tendinitis, rotator cuff tear, frozen shoulder, and degenerative arthritis, but are not limited thereto.

The pharmaceutical composition may exhibit an immunomodulatory or anti-inflammatory effect.

In a preferred embodiment, the sex hormone formulation is an injection.

Insufficiency or deficit of sex hormones causes women to suffer from menstrual irregularity and dysmenorrhea, irregular menstrual cycles, insufficient height and breast development, skin troubles, hypoactive sexual desire disorder and anorgasmia, reduced vaginal contraction, premature menopause and menopausal disorder, skin senescence, depression, nervousness, dyspareunia, urinary incontinence, decreased vaginal discharges, menopause, osteoporosis, infertility, and various female disorders and causes hypoactive sexual desire disorder, hypogonadism, a sensation of fatigue, depression, lethargy, decreased muscle, dynapenia, abdominal obesity, skin senescence, a decrease of bone density, and memory decline in men, without limitations thereto.

Advantageous Effects

The present disclosure pertains to biodegradable polymer microparticles bearing a drug and a preparation method therefor. In the method, a steroid drug and a biodegradable polyester-based polymer are dissolved in an organic solvent and sprayed into a low-temperature hydrocarbon solution to form frozen microparticles that are then immersed in a low-temperature, aqueous salt solution to deprive the microparticles of the organic solvent, thereby preparing biodegradable polymer microparticles bearing a steroid drug. The steroid drug-bearing biodegradable polymer microparticles were found to have excellent biocompatibility, biodegradability, porosity, and mechanical strength and to release the steroid drug for a long period of time.

Accordingly, the biodegradable polymer microparticles bearing a drug according to the present disclosure are expected to be used to develop a drug delivery system that can steadily release the drug over at least one month after one injection dose to treat a symptom or disease caused by the insufficiency or deficit of a sex hormone, with minimum side effects.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

Example 1: Preparation of Steroid Drug-Bearing Biodegradable Polymer Microparticles Use was made of the anti-inflammatory drug triamcinolone as a steroid drug, poly(lactic-co-glycolic acid) (PLGA) as a biodegradable polyester-based polymer, and DMSO (dimethyl sulfoxide) as an organic solvent.

In 500 ml of DMSO, 1 g of triamcinolone and 20 g of PLGA having a weight average molecular weight of 110,000 and a ratio of 75:25 of lactic acid:glycolic acid were dissolved to give a 4.2% (w/v) solution of the drug/biodegradable polymer mixture. The drug/biodegradable polymer mixture solution was sprayed at a rate of 1.0 g/min, together with air at a rate of 5.0 l/min, into n-hexane chilled to −5° C. The sprayed drug/biodegradable polymer mixture solution was frozen into spheres in the chilled n-hexane to form microparticles.

The frozen microparticles thus obtained were left for 72 hours in 1,000 ml of a 25% (w/v) aqueous NaCl solution chilled to −20° C. to remove the DMSO, followed by filtration to obtain DMSO-free microparticles having the drug and the biodegradable polymer mixed therein.

The microparticles were washed with 5,000 ml of distilled water and filtered to remove residual DMSO and NaCl, followed by lyophilization to prepare biodegradable polymer microparticles bearing a steroid drug.

Example 2: Physical Characterization of Steroid Drug-Bearing Biodegradable Polymer Microparticles For physical characterization, the steroid drug-bearing biodegradable polymer microparticles prepared in Example 1 were examined for size, morphology, surface, and inner states by electron microscopy, and the results are given in FIG. 1.

In addition, the production yield of the steroid drug-bearing biodegradable polymer microparticles was calculating by measuring the amount of finally obtained microparticles relative to that of the polymer fed, and the results are given in Table 1, below.

TABLE 1

| Spraying Condition | | | | |
|---|---|---|---|---|
| Drug-mixed polymer solution (%, w/v) | Spray solution (g/min) | Spray air (g/min) | Microparticle size (μm) | Yield (%) |
| 4.2 | 1.0 | 5 | ≤100 | 62 |

Figure 1:
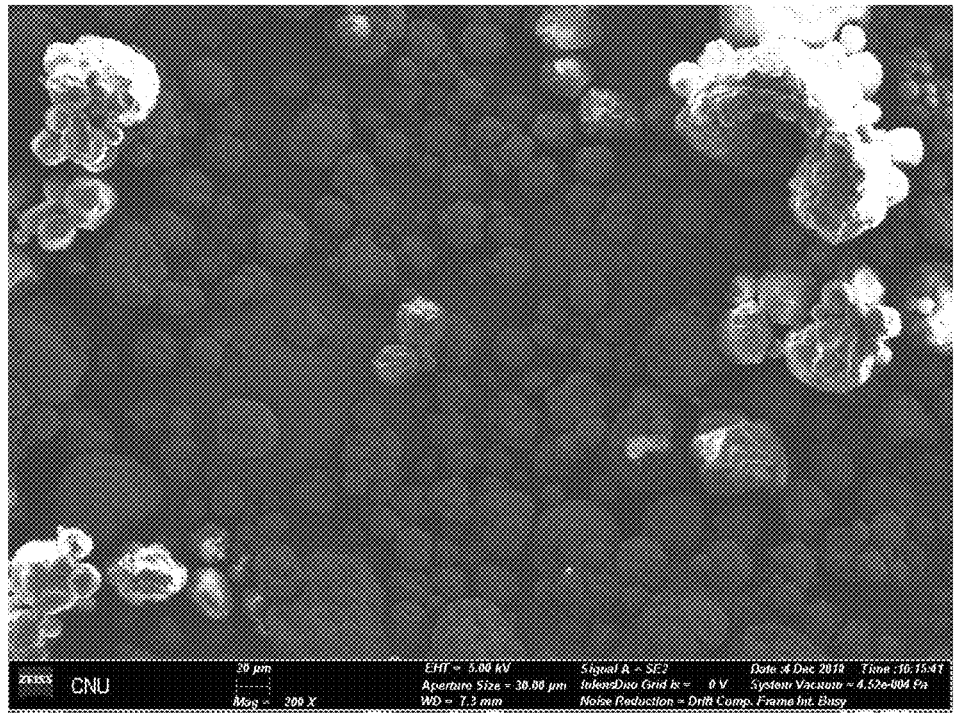
FIG. 1 shows sizes of the steroid drug-bearing biodegradable polymer microparticles prepared according to the preparation method of the present disclosure, as measured by electron microscopy (×200; polymer solution 4.2% (w/v); polymer solution spray rate: 1.0 g/min; air spray rate: 5 l/min).

As can be seen in FIG. 1 and Table 1, the steroid drug-bearing biodegradable polymer microparticles prepared in Example 1 were measured to have a size of 100 μm or less.

Figure 2:
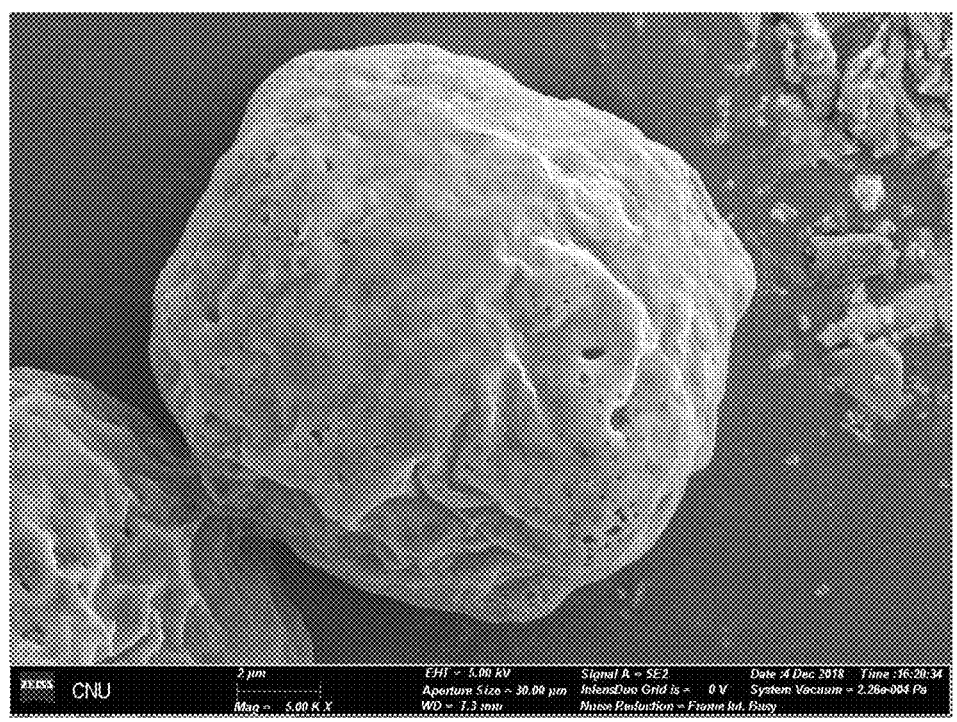
FIG. 2 shows appearances of the steroid drug-bearing biodegradable polymer microparticles prepared according to the preparation method of the present disclosure, as observed by electron microscopy (×5,000; polymer solution 4.2% (w/v); polymer solution spray rate: 1.0 g/min; air spray rate: 5 l/min).
Figure 3:
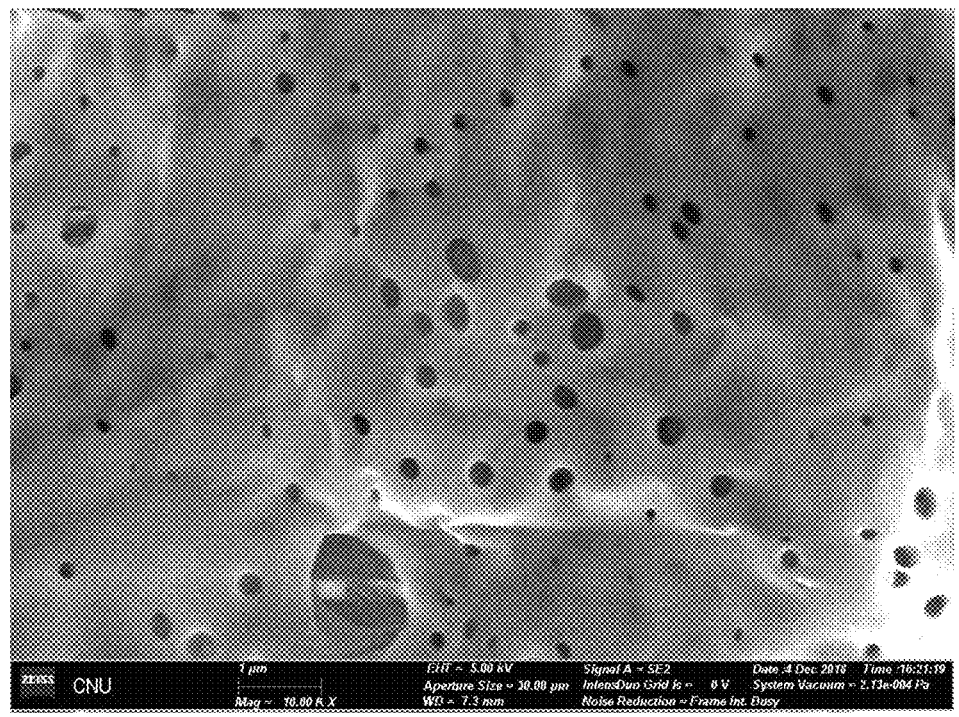
FIG. 3 shows the surface of the steroid drug-bearing biodegradable polymer microparticles prepared according to the preparation method of the present disclosure, as observed by electron microscopy (×10,000; polymer solution 4.2% (w/v); polymer solution spray rate: 1.0 g/min; air spray rate: 5 l/min).
Figure 4:
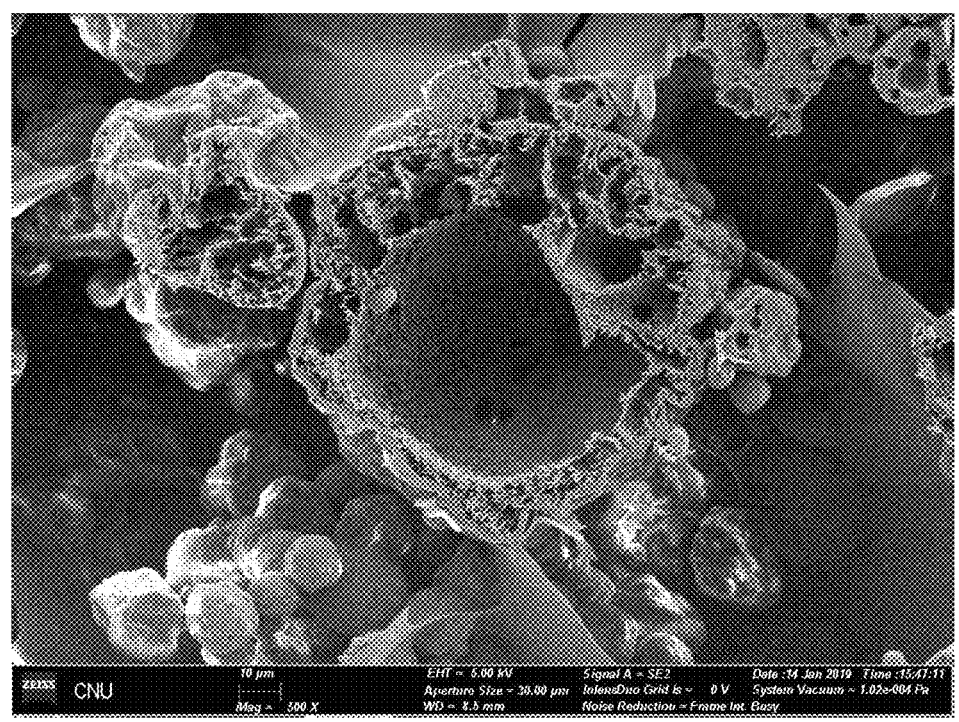
FIG. 4 shows the inner structure of the steroid drug-bearing biodegradable polymer microparticles prepared according to the preparation method of the present disclosure, as observed by electron microscopy (×500; polymer solution 4.2% (w/v); polymer solution spray rate: 1.0 g/min; air spray rate: 5 l/min).
Figure 5:
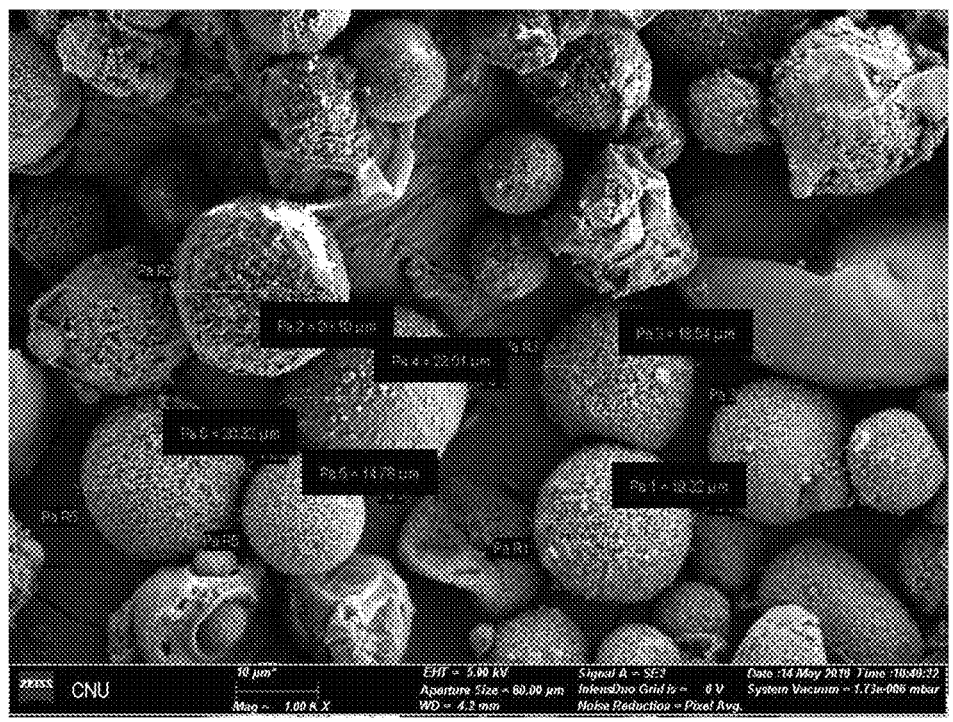
FIG. 5 shows sizes of the sex hormone drug-bearing biodegradable polymer microparticles (progesterone, testosterone, PLGA 50:50) prepared according to the preparation method of the present disclosure, as measured by electron microscopy (×1,000; polymer solution 12.0% (w/v); polymer solution spray rate: 1.0 g/min; air spray rate: 5 l/min).
Figure 6:
FIG. 6 shows appearances of the sex hormone drug-bearing biodegradable polymer microparticles (progesterone, testosterone, PLGA 50:50) prepared according to the preparation method of the present disclosure, as measured by electron microscopy (×3,000; polymer solution 12.0% (w/v); polymer solution spray rate: 1.0 g/min; air spray rate: 5l/min).
Figure 7:
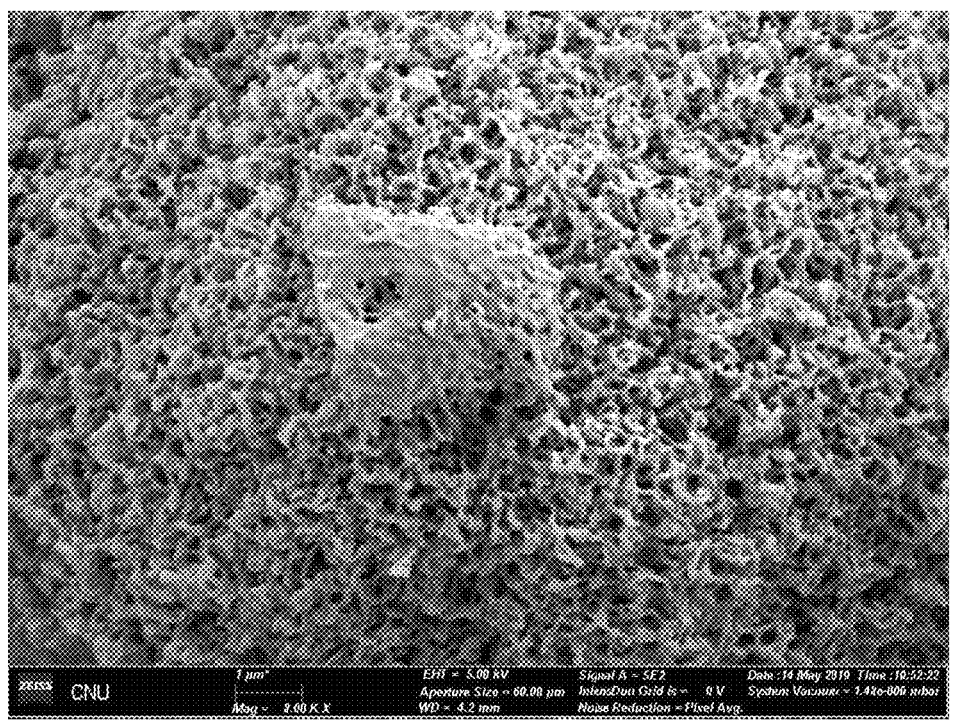
FIG. 7 shows the surface of the sex hormone drug-bearing biodegradable polymer microparticles (progesterone, testosterone, PLGA 50:50) prepared according to the preparation method of the present disclosure, as measured by electron microscopy (×8,000; polymer solution 12.0% (w/v); polymer solution spray rate: 1.0 g/min; air spray rate: 5l/min).
Figure 8:
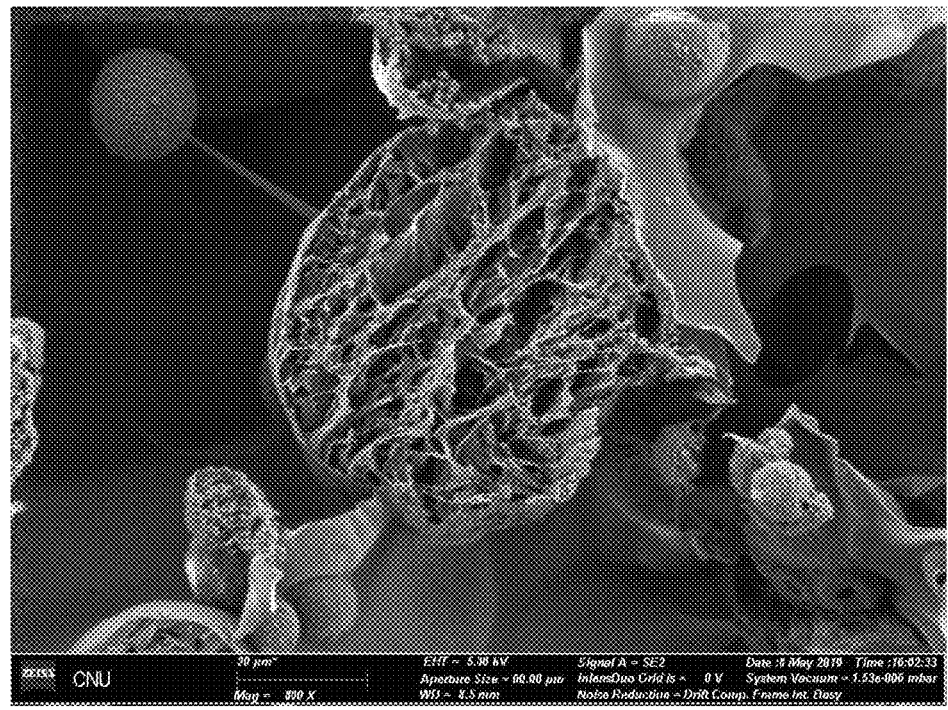
FIG. 8 shows the inner structure of the sex hormone drug-bearing biodegradable polymer microparticles (progesterone, testosterone, PLGA 50:50) prepared according to the preparation method of the present disclosure, as measured by electron microscopy (×300; polymer solution 12.0% (w/v); polymer solution spray rate: 1.0 g/min; air spray rate: 5l/min).
Figure 9:
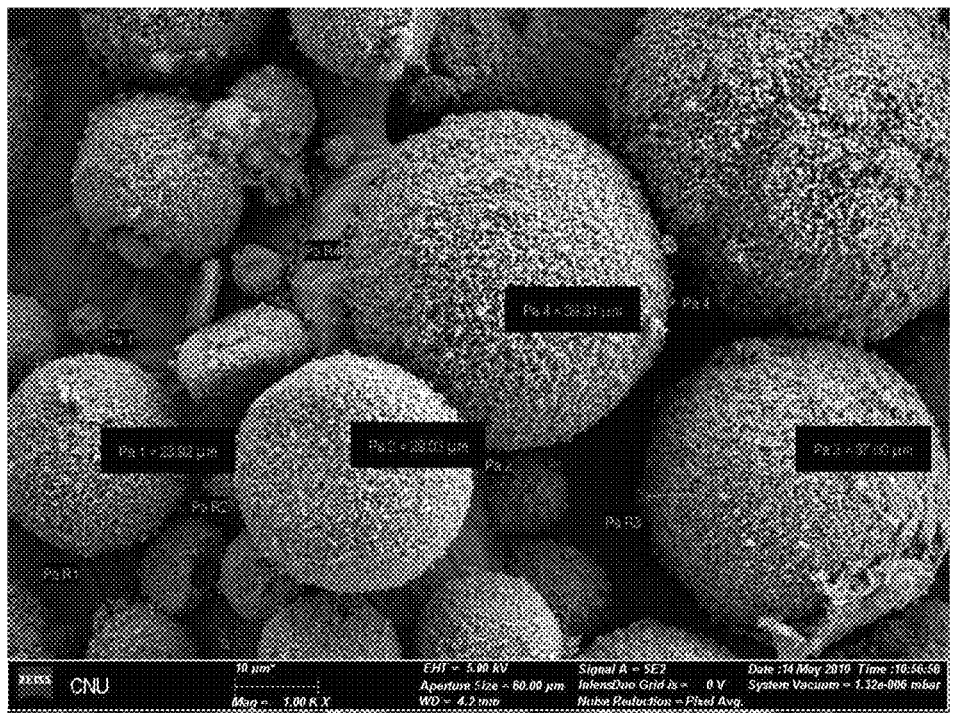
FIG. 9 shows sizes of the sex hormone drug-bearing biodegradable polymer microparticles (ethynyl estradiol, PLGA 50:50) prepared according to the preparation method of the present disclosure, as measured by electron microscopy (×1,000; polymer solution 12.0% (w/v); polymer solution spray rate: 1.0 g/min; air spray rate: 5l/min).
Figure 10:
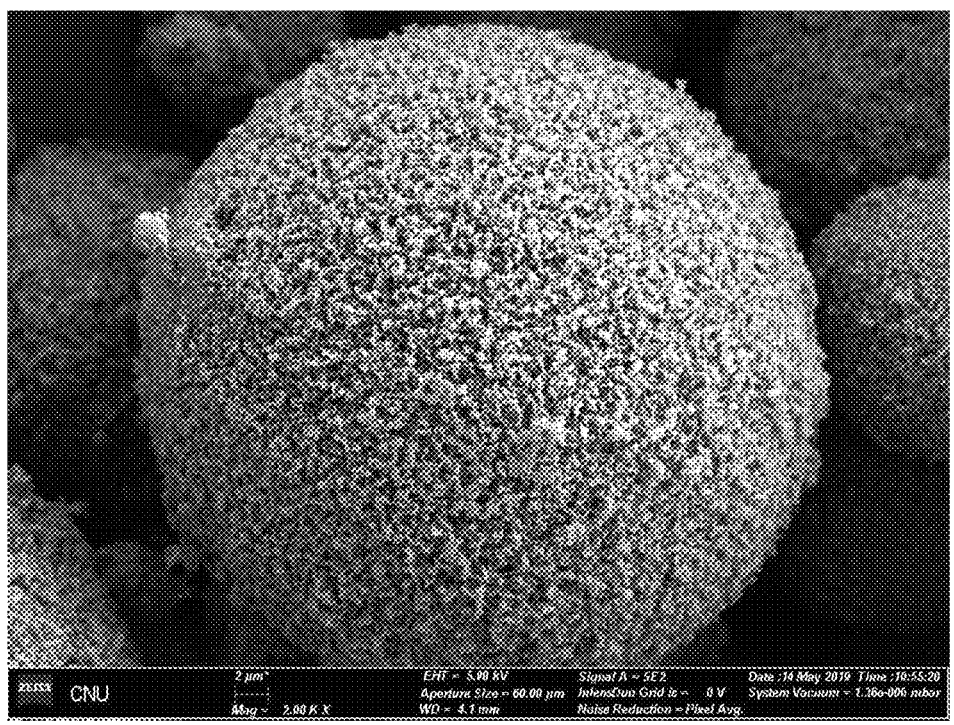
FIG. 10 shows appearances of the sex hormone drug-bearing biodegradable polymer microparticles (ethynyl estradiol, PLGA 50:50) prepared according to the preparation method of the present disclosure, as measured by electron microscopy (×2,000; polymer solution 12.0% (w/v); polymer solution spray rate: 1.0 g/min; air spray rate: 5l/min).
Figure 11:
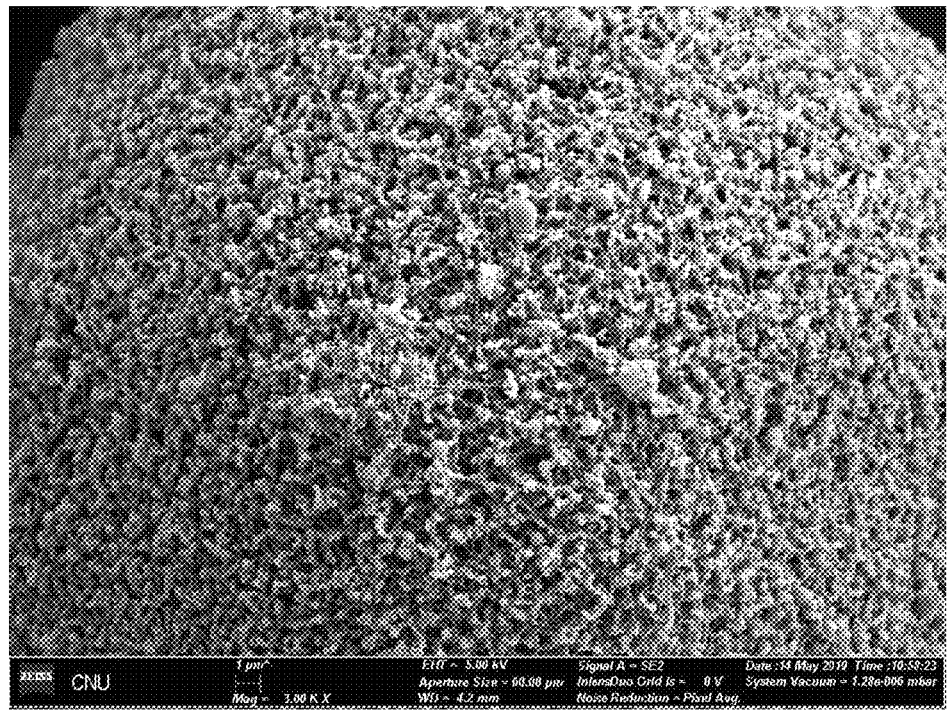
FIG. 11 shows the surface of the sex hormone drug-bearing biodegradable polymer microparticles (ethynyl estradiol, PLGA 50:50) prepared according to the preparation method of the present disclosure, as measured by electron microscopy (×3,000; polymer solution 12.0% (w/v); polymer solution spray rate: 1.0 g/min; air spray rate: 5l/min).
Figure 12:
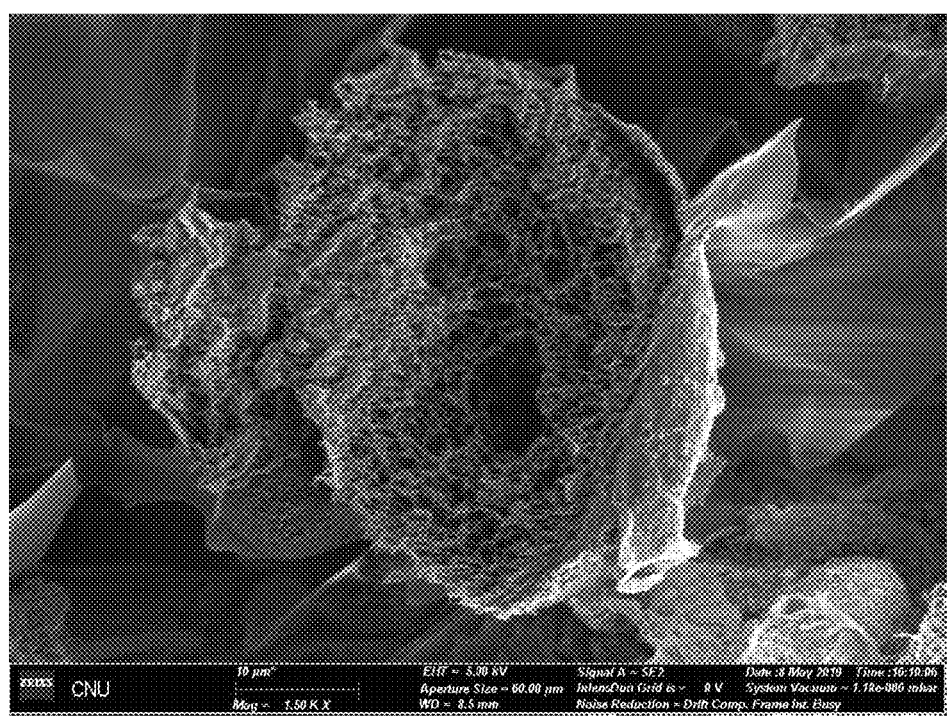
FIG. 12 shows the inner structure of the sex hormone drug-bearing biodegradable polymer microparticles (ethynyl estradiol, PLGA 50:50) prepared according to the preparation method of the present disclosure, as measured by electron microscopy (×1,500; polymer solution 12.0% (w/v); polymer solution spray rate: 1.0 g/min; air spray rate: 5l/min).
Figure 13:
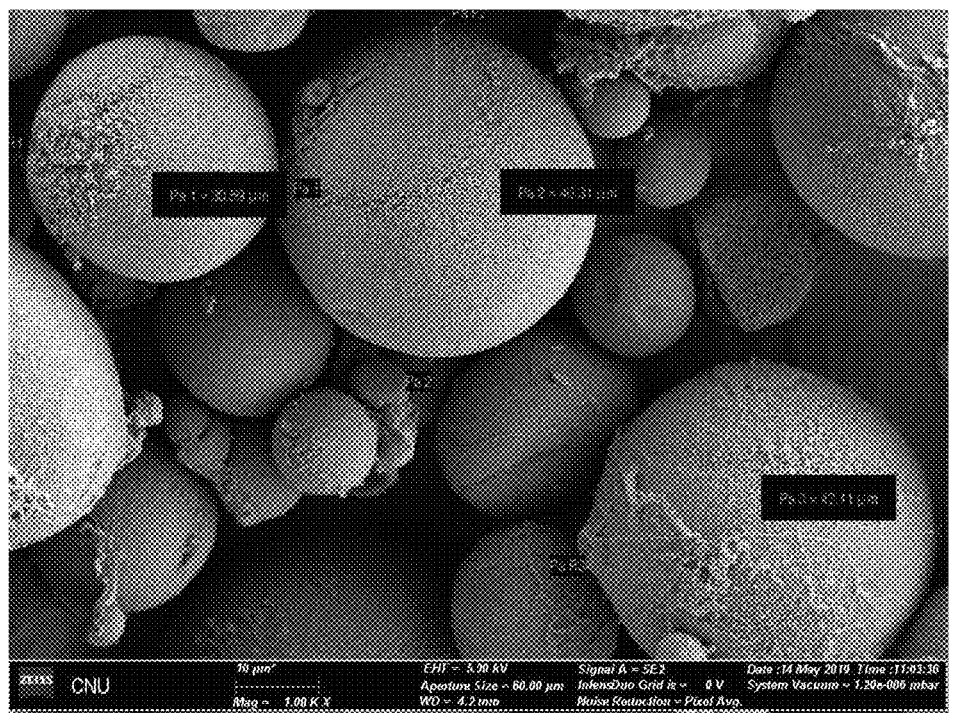
FIG. 13 shows sizes of the sex hormone drug-bearing biodegradable polymer microparticles (progesterone, testosterone, PDLLA) prepared according to the preparation method of the present disclosure, as measured by electron microscopy (×1,000; polymer solution 9.0% (w/v); polymer solution spray rate: 1.0 g/min; air spray rate: 5l/min).
Figure 14:
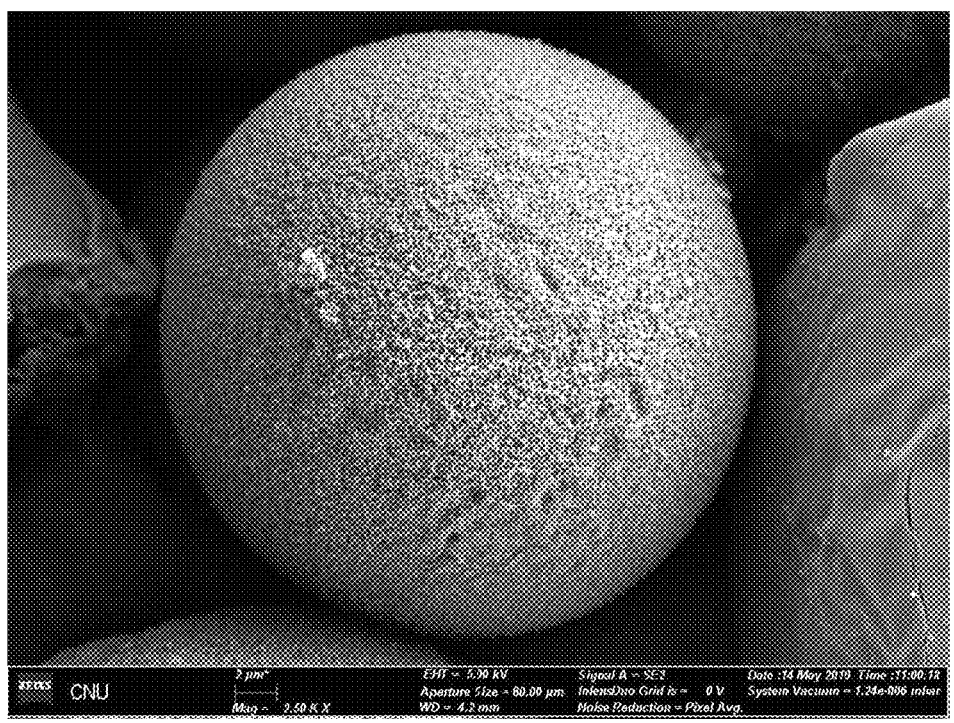
FIG. 14 shows appearances of the sex hormone drug-bearing biodegradable polymer microparticles (progesterone, testosterone, PDLLA) prepared according to the preparation method of the present disclosure, as measured by electron microscopy (×2,500; polymer solution 9.0% (w/v); polymer solution spray rate: 1.0 g/min; air spray rate: 5 l/min).
Figure 15:
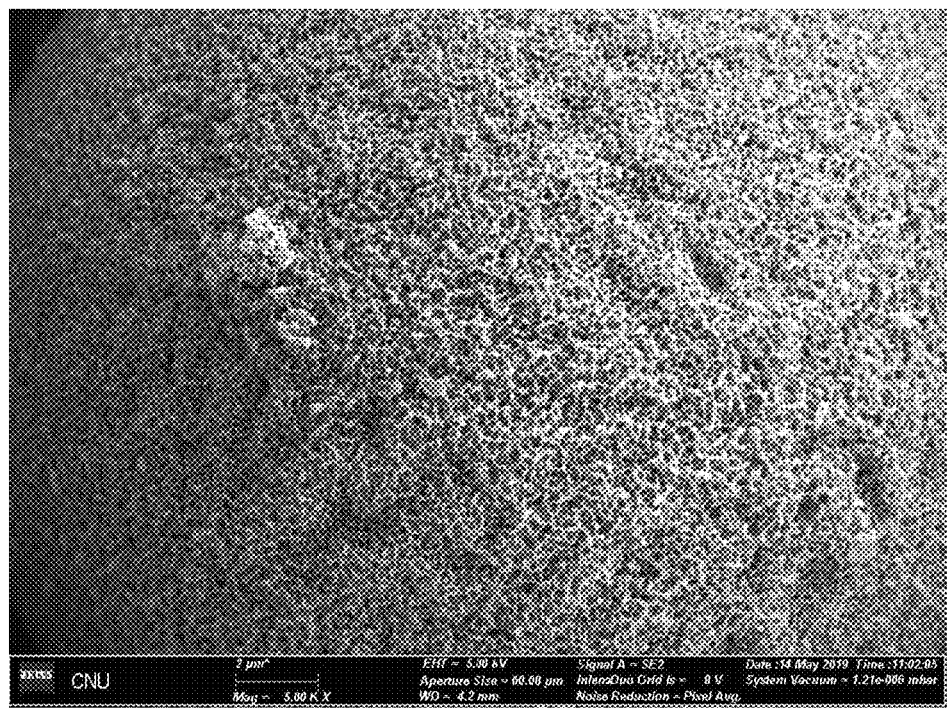
FIG. 15 shows the surface of the sex hormone drug-bearing biodegradable polymer microparticles (progesterone, testosterone, PDLLA) prepared according to the preparation method of the present disclosure, as measured by electron microscopy (×5,000; polymer solution 9.0% (w/v); polymer solution spray rate: 1.0 g/min; air spray rate: 5 l/min).
Figure 16:
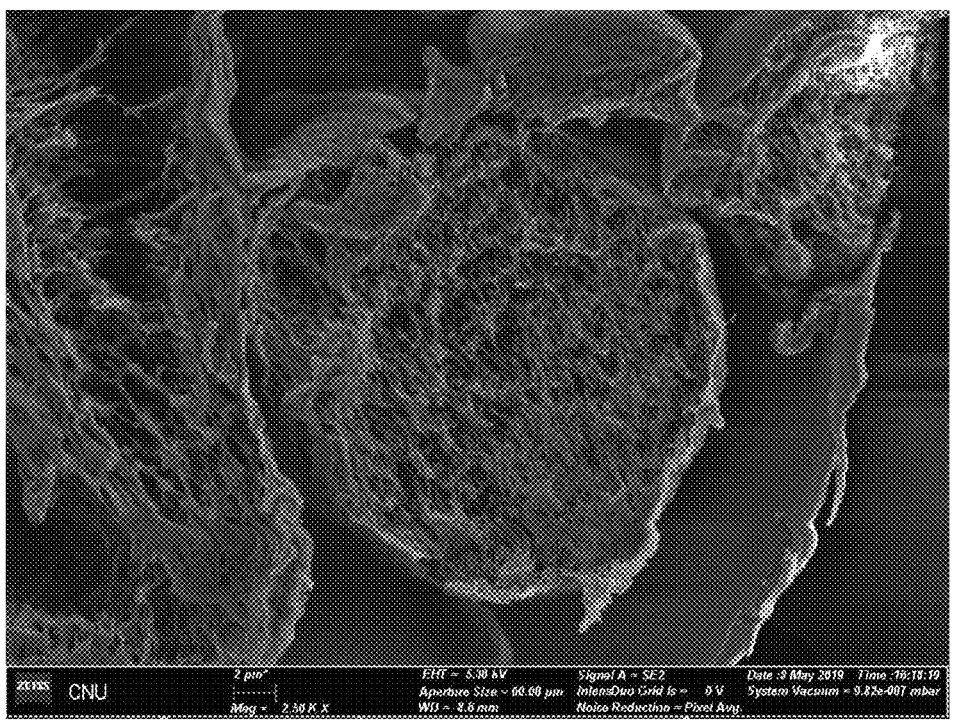
FIG. 16 shows the inner structure of the sex hormone drug-bearing biodegradable polymer microparticles (progesterone, testosterone, PDLLA) prepared according to the preparation method of the present disclosure, as measured by electron microscopy (×2,500; polymer solution 9.0% (w/v); polymer solution spray rate: 1.0 g/min; air spray rate: 5 l/min).
Figure 17:
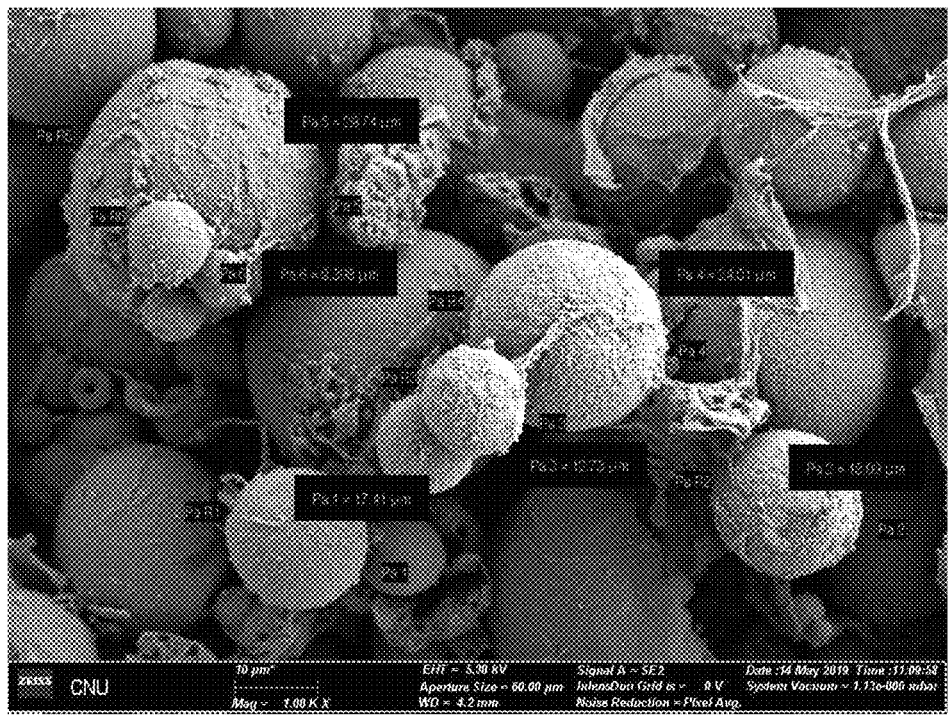
FIG. 17 shows sizes of the sex hormone drug-bearing biodegradable polymer microparticles (ethynyl estradiol, PDLLA) prepared according to the preparation method of the present disclosure, as measured by electron microscopy (×1,000; polymer solution 9.0% (w/v); polymer solution spray rate: 1.0 g/min; air spray rate: 5 l/min).
Figure 18:
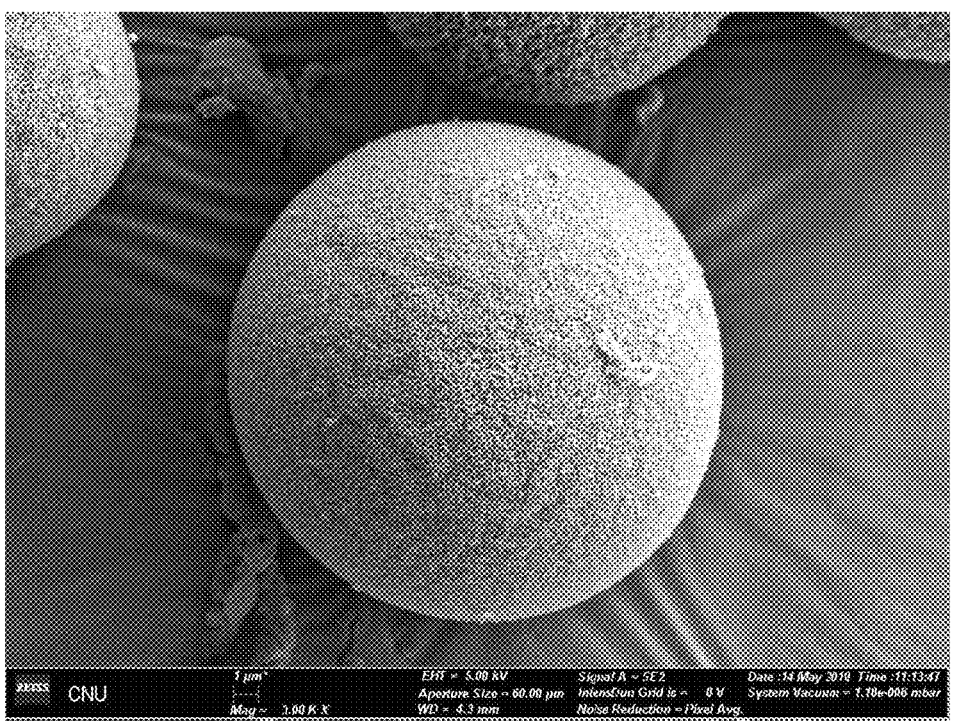
FIG. 18 shows appearances of the sex hormone drug-bearing biodegradable polymer microparticles (ethynyl estradiol, PDLLA) prepared according to the preparation method of the present disclosure, as measured by electron microscopy (×3,000; polymer solution 9.0% (w/v); polymer solution spray rate: 1.0 g/min; air spray rate: 5 l/min).
Figure 19:
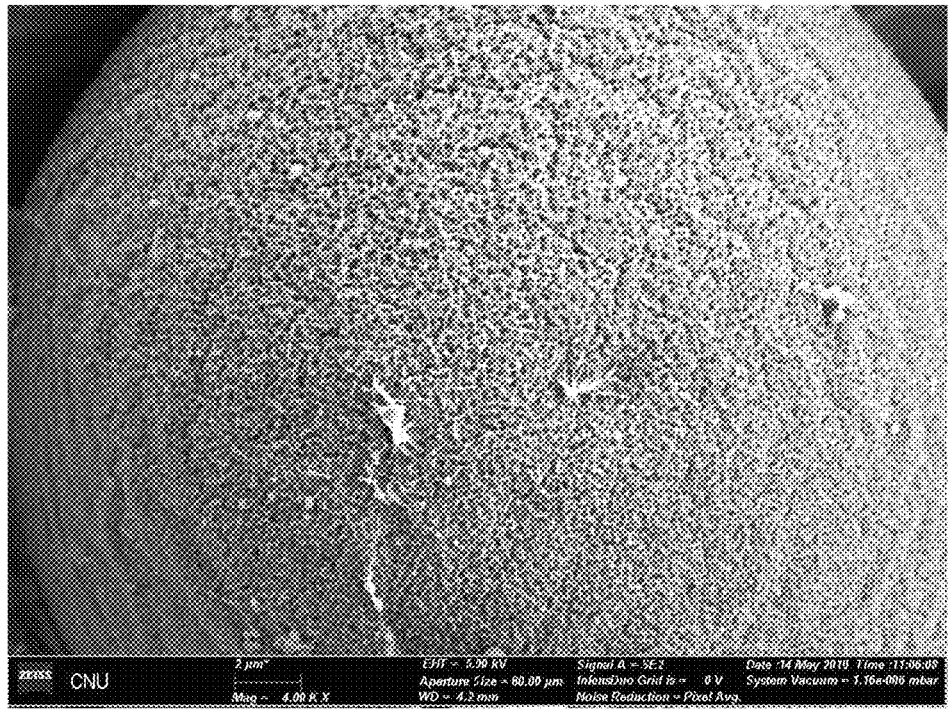
FIG. 19 shows the surface of the sex hormone drug-bearing biodegradable polymer microparticles (ethynyl estradiol, PDLLA) prepared according to the preparation method of the present disclosure, as measured by electron microscopy (×4,000; polymer solution 9.0% (w/v); polymer solution spray rate: 1.0 g/min; air spray rate: 5 l/min).
Figure 20:
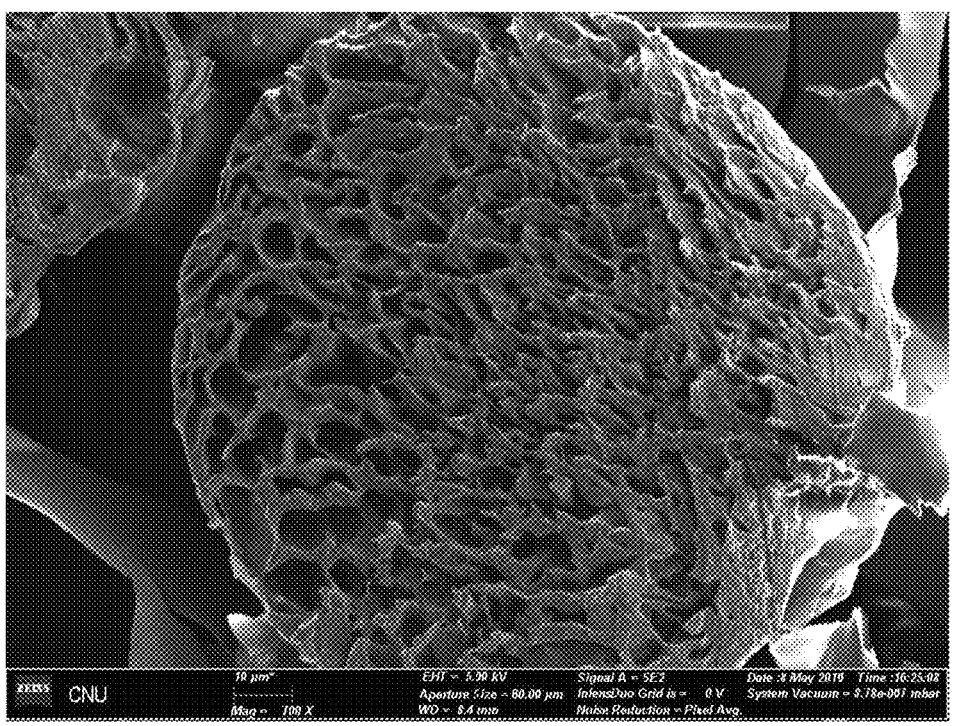
FIG. 20 shows the inner structure of the sex hormone drug-bearing biodegradable polymer microparticles (ethynyl estradiol, PDLLA) prepared according to the preparation method of the present disclosure, as measured by electron microscopy (×700; polymer solution 9.0% (w/v); polymer solution spray rate: 1.0 g/min; air spray rate: 5 l/min).

In addition, FIG. 2 shows appearances of the steroid drug-bearing biodegradable polymer microparticles prepared in Example 1. As can be seen in FIG. 2, the microparticles were spherical. The electron microscopic image of the surface in FIG. 3 indicates that the prepared microparticles are porous. Furthermore, the microparticles were observed to be hollow as seen in the microparticle inside image of FIG. 4.

The data thus obtained demonstrate that the steroid drug-bearing biodegradable polymer microparticles prepared using the preparation method of the present disclosure have sizes suitable to be administered through a syringe into the body and are economically beneficial in terms of yield.

Examples 3-6: Preparation of Sex Hormone Drug-Bearing Biodegradable Polymer Microparticles In the case where the steroid drug is a sex hormone, biodegradable polymer microparticles bearing sex hormones were prepared by using progesterone (Tokyo Chemical industry, CAS. NO. 57-83-0/$C_{21}H_{30}O_2$), testosterone (Tokyo Chemical industry, CAS. NO. 57-85-2/$C_{22}H_{32}O_3$), and ethynyl estradiol (Tokyo Chemical industry, CAS. NO. 57-63-6/$C_{20}H_{24}O_2$) as sex hormones and poly(D,L-lactic-co-glycolic acid) (PLGA) and poly-D,L-lactide (PDLLA) as biodegradable polymers.

The sex hormone drugs and biodegradable polymers listed in Table 2, below, were mixed with DMSO (dimethyl sulfoxide) to give drug/biodegradable polymer mixture solutions. Each of the drug/biodegradable polymer mixture solutions was sprayed at a rate of 1.0 g/min, together with air at a spray rate of 5.0 l/min, into n-hexane chilled to −5° C. The drug/biodegradable polymer mixture solutions were frozen into spheres in the chilled n-hexane to form frozen microparticles.

After being harvested, the frozen microparticles were left for 72 hours in 1,000 ml of a 25% (w/v) aqueous NaCl solution chilled to −20° C. to deprive the microparticles of the DMSO ingredient, followed by filtration to obtain DMSO-removed microparticles in which the drugs and the biodegradable polymer were mixed. The microparticles were washed with 5,000 ml of distilled water and filtered to remove residual DMSO and NaCl. Thereafter, lyophilization afforded biodegradable polymer microparticles bearing sex hormone drugs according to the present disclosure.

TABLE 2

| Example # | Sex Hormone Drug Kind | Content (g) | Biodegradable Polymer Kind | Content (g) | DMSO (ml) |
|---|---|---|---|---|---|
| 3 | Progesterone Testosterone | 1.4 0.6 | PLGA with weight average molecular weight of 72,000 | 20 | 183 |
| 4 | Ethynyl estradiol | 0.6 | PLGA with weight average molecular weight of 33,000 | 21.4 | 183 |
| 5 | Progesterone Testosterone | 1.4 0.6 | PDLLA with weight average molecular weight of 103,000 | 20 | 244 |
| 6 | Ethynyl estradiol | 0.6 | PDLLA with weight average molecular weight of 103,000 | 21.4 | 244 |

Experimental Example 1: Physical Characterization of Sex Hormone Drug-Bearing Biodegradable Polymer Microparticles For physical characterization, the sex hormone drug-bearing biodegradable polymer microparticles prepared in Examples 3-6 were examined for size, morphology, surface, and inner states by electron microscopy, and the results are given in FIGS. 5-20.

In addition, production yields of the sex hormone drug-bearing biodegradable polymer microparticles were calculating by measuring the amounts of finally obtained microparticles relative to those of the polymers fed. Before the calculation, the finally obtained microparticles were filtered via a sieve (CISA, 100 µm sieve). The results are given in Table 3, below.

TABLE 3

| | Spraying Condition | | | | |
|---|---|---|---|---|---|
| Example # | Drug-mixed polymer solution (%, w/v) | Spray solution (g/min) | Spray air (l/min) | Micro-particle size (µm) | Yield (%) |
| 3 | 12.0 | 1.0 | 5.0 | ≤100 | 64.3 |
| 4 | 12.0 | 1.0 | 5.0 | ≤100 | 64.7 |
| 5 | 9.0 | 1.0 | 5.0 | ≤100 | 63.4 |
| 6 | 9.0 | 1.0 | 5.0 | ≤100 | 63.1 |

As can be seen in FIGS. 5, 9, 13, and 17 and Table 3, the sex hormone drug-bearing biodegradable polymer microparticles prepared in Examples 3-6 were measured to have a size of 100 µm or less.

In addition, FIGS. 6, 10, 14, and 18 show appearances of the sex hormone drug-bearing biodegradable polymer microparticles prepared in Examples 3-6. As can be seen in the figures, the microparticles were spherical. The electron microscopic images of the surfaces in FIGS. 7, 11, 15, and 19 indicate that the prepared microparticles are porous. Furthermore, the microparticles were observed to be hollow as seen in the microparticle inside image of FIGS. 8, 12, 16, and 20.

The data thus obtained demonstrate that the sex hormone drug-bearing biodegradable polymer microparticles prepared using the preparation method of the present disclosure have sizes suitable to be administered through a syringe into the body and are economically beneficial in terms of yield.

Experimental Example 2: Identification of Sex Hormone Drug Borne by in Biodegradable Polymer Microparticles and Drug Release from Microparticles Of the sex hormone drug-bearing biodegradable polymer microparticles prepared in Examples 3-6, the microparticles of Example 4 (ethynyl estradiol and PLGA 50:50) were examined to see whether the drug (ethynyl estradiol) borne by the microparticles was the same as the pure drug (ethynyl estradiol).

Figure 21:
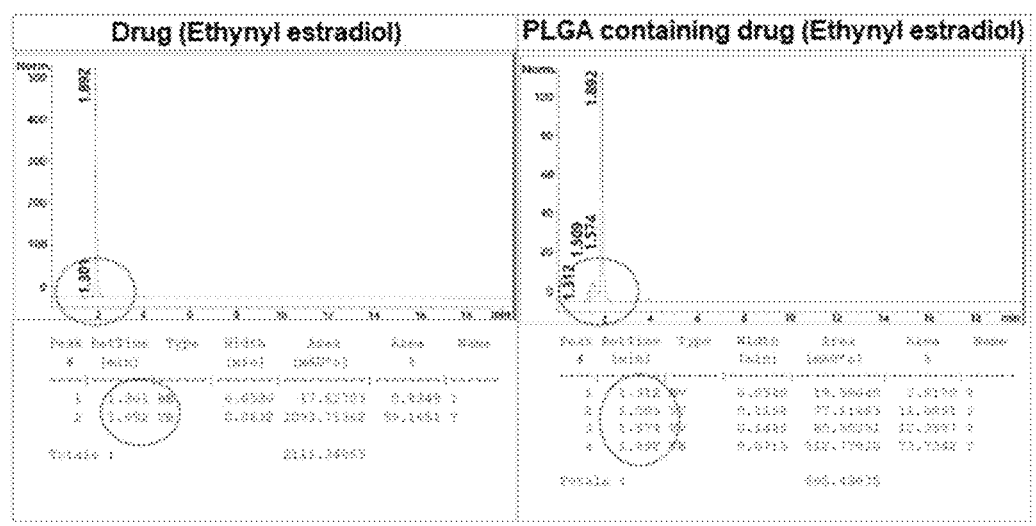
FIG. 21 shows HPLC chromatograms indicating whether the sex hormone drug-bearing biodegradable polymer microparticles prepared in Example 4 (ethynyl estradiol, PLGA 50:50) release the same as the pure drug (ethynyl estradiol).

In 10 ml of physiological saline, 0.1 g of the pure drug (ethynyl estradiol) or 0.1 g of the PLGA microparticles prepared in Example 4 was dissolved. The solutions were shaken for 10 min on a shaker roller and incubated for 12 hours in a 37° C. incubator, followed by characterization of the drug through HPLC (HP 1260, liquid chromatography/ACN 80:Water 20/1.0 ml (min)/20 µl/25° C./275 nm). The results are depicted in FIG. 21. As seen in FIG. 21, the drug (ethynyl estradiol) was identified to be the same as the drug (ethynyl estradiol) bore in the PLGA microparticles of Example 4.

Figure 22:
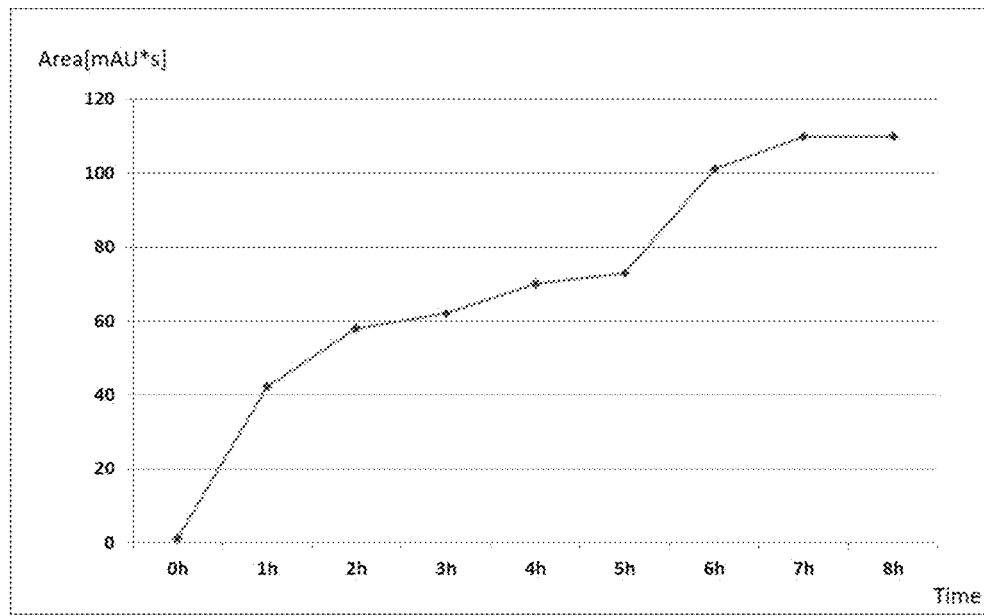
FIG. 22 show the drug release behavior of the sex hormone drug-bearing biodegradable polymer microparticles prepared in Example 4 (ethynyl estradiol, PLGA 50:50) over time, as monitored by HPLC.
Figure 22:
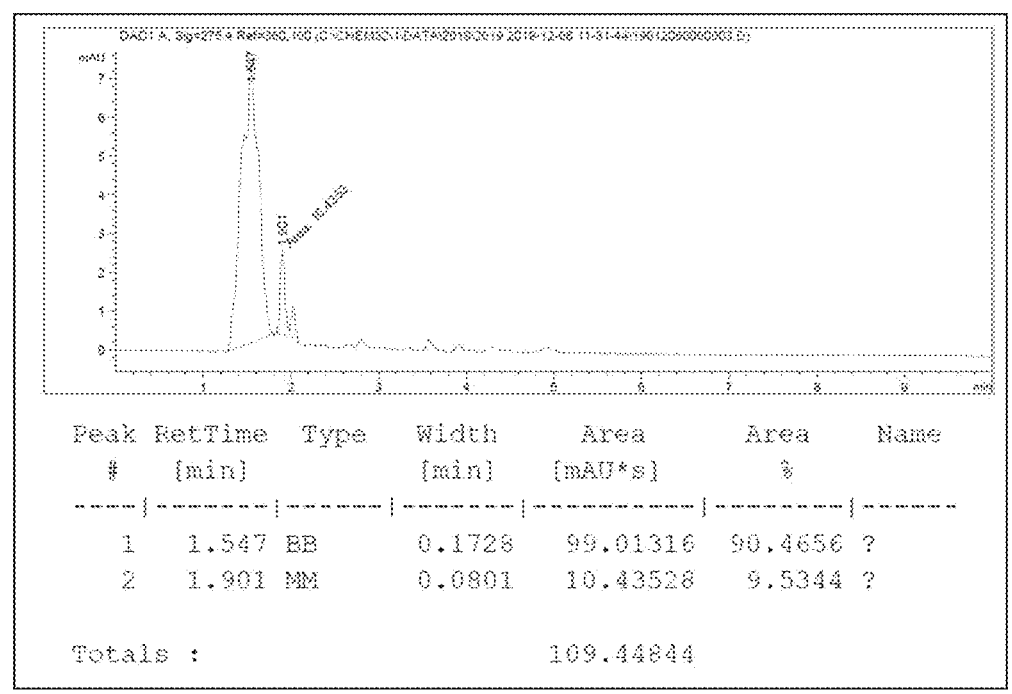

The sex hormone drug-bearing polymer microparticles prepared in Example 4 (ethynyl estradiol and PLGA 50:50) were measured for drug release behavior over time. In this regard, a solution of 1 g of the PLGA microparticles in 10 ml of physiological saline was placed on a shaker roller and agitated at a speed of 50 rpm to extract the drug at a rate of 1 ml per hour. The entire solvent was exchanged with a fresh one every hour for accurate drug release. Temporal drug release behavior was monitored using HPLC (HP 1260, liquid chromatography/ACN 80:Water 20/1.0 ml (min)/20 µl/25° C./275 nm)). The results are depicted in FIG. 22. As seen in FIG. 22, the microparticles were found to release the drug at constant rates, without a burst of release at the initial stage.

As described hitherto, the microparticles are prepared from a solution of a polymer and a drug in DMSO during which the polymer and the drug are bound to each other, whereby the drug can be released at constant rates depending on the content of the drug and the degradation rate of the polymer. Compared to conventional approaches in which polymeric particles are mixed with a drug, together with an adhesive, to adsorb the drug onto the surface of the particles or polymeric particles are immersed in a drug solution to allow the drug to permeate into the particles, the present disclosure can steadily release the drug depending on polymer degradation speed and drug content.

The invention claimed is:

1. A method for preparing biodegradable polymeric microparticles bearing a steroid drug, the method comprising the steps of:
   (a) dissolving a mixture of a steroid drug and a biodegradable polyester-based polymer in dimethylsulfoxide (DMSO) to prepare a solution containing the steroid drug and the biodegradable polyester-based polymer;
   (b) spraying the solution containing the steroid drug and the biodegradable polyester-based polymer into a C5-10 hydrocarbon solution maintained at a temperature of −10 to −5° C. to form microparticles;
   (c) adding the microparticles to an aqueous salt solution to dissolve and eliminate the DMSO; and
   (d) desalting the DMSO eliminated microparticles,
   wherein the mixture of the steroid drug and the biodegradable polyester-based polymer in step (a) comprises the steroid drug and the biodegradable polyester-based polymer at a weight ratio of 1:99 to 3:7 and is dissolved in an amount of 1-25% (w/v) in DMSO, based on the total volume of the solution,
   wherein the C5-10 hydrocarbon solution in step (b) is at least one selected from the group consisting of pentane, hexane, heptane, octane, nonane, decane, and petroleum ether,
   wherein the aqueous salt solution in step (c) is a 5-30% (w/v) solution of NaCl or $CaCl_2$) in water,
   wherein the biodegradable polyester-based polymer is poly(D,L-lactic-co-glycolic acid)(PLGA), and
   wherein the biodegradable polymeric microparticles bearing a steroid drug are spherical porous microparticles having a diameter of 10-100 μm, and steadily release the steroid drug over at least one month.

2. The method of claim 1, wherein the biodegradable polyester-based polymer has a weight average molecular weight of 10,000 to 250,000.

3. The method of claim 1, wherein the steroid drug is at least one selected from the group consisting of deflazacort, desonide, desoximetasone, dexamethasone, diflorasone, diflucortolone, difluprednate, loteprednol etabonate, rimexolone, mazipredone, medrysone, methylprednisolone, meprednisone, mometasone furoate, beclomethasone, betamethasone, budesonide, algestone, alclometasone, amcinonide, enoxolone, corticosterone, cortisone, cortivazol, chloroprednisone, clobetasol, clobetasone, clocortolone, cloprednol, tixocortol, triamcinolone, triamcinolone acetonide, triamcinolone benetonide, triamcinolone hexacetonide, paramethasone, pregnenolone acetate, prednicarbate, prednisolone, prednisolone 25-diethylaminoacetate, prednisolone sodium phosphate, prednisone, prednival, prednylidene, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, and a sex hormone.

4. The method of claim 3, wherein the sex hormone is at least one selected from the group consisting of progesterone, testosterone, estrogen, androgen, estradiol, levonorgestrel, gestodene, desogestrel, dienogest, cyproterone acetate, and ethynyl estradiol.

* * * * *